(12) United States Patent
Kaufman

(10) Patent No.: US 6,534,487 B1
(45) Date of Patent: *Mar. 18, 2003

(54) METHODS FOR SUPPRESSING APPETITE AND ENHANCING EXERCISE AND RECOVERY

(75) Inventor: Francine R. Kaufman, Los Angeles, CA (US)

(73) Assignee: Childrens Hospital Los Angeles, Los Angeles, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/368,063

(22) Filed: Aug. 3, 1999

(51) Int. Cl.$^7$ .............................................. A61K 31/715
(52) U.S. Cl. ........................... 514/60; 514/54; 514/866; 426/808; 424/439; 424/441
(58) Field of Search ........................... 514/60, 54, 866; 426/808; 424/439, 441

(56) References Cited

U.S. PATENT DOCUMENTS

| | | | |
|---|---|---|---|
| 3,619,209 A | 11/1971 | Hegadorn et al. ............. | 99/139 |
| 3,969,514 A | 7/1976 | Tiemstra ..................... | 426/90 |
| 4,496,606 A | 1/1985 | Michnowski ................ | 426/658 |
| 4,629,725 A | 12/1986 | Hiji .............................. | 514/60 |
| 4,921,877 A | 5/1990 | Cashmere et al. .......... | 514/866 |
| 5,097,023 A | 3/1992 | Ducep et al. ............... | 536/17.4 |
| 5,169,662 A | 12/1992 | Spicer et al. ............... | 426/449 |
| 5,232,733 A | 8/1993 | Resmer ...................... | 426/590 |
| 5,356,879 A | 10/1994 | Zehner et al. ................ | 514/25 |
| 5,605,893 A | 2/1997 | Kaufman .................... | 514/60 |
| 5,843,921 A * | 12/1998 | Kaufman .................... | 514/60 |
| 5,866,555 A * | 2/1999 | Bell et al. ..................... | 514/60 |
| 5,902,797 A * | 5/1999 | Bell et al. ..................... | 514/53 |

FOREIGN PATENT DOCUMENTS

| | | | |
|---|---|---|---|
| EP | 0 443 789 A1 | 8/1991 | ............. A23L/1/30 |
| EP | 0 504 055 A1 | 9/1992 | ............. A23L/1/09 |
| WO | WO 95/24906 | 9/1995 | ......... A61K/31/715 |
| WO | WO 96/31129 | 10/1996 | ............. A23L/1/29 |
| WO | WO 98/17286 | 4/1998 | ......... A61K/31/715 |

OTHER PUBLICATIONS

Behall et al., Effect of starch structure on glucose and insulin responses in adults, *Am. J. Clin. Nutr.,* 47:428–432 (1988).
Boneh et al., Raw cornstarch as an additional therapy in nesidioblastosis, *Am. J. Clin. Nutr.,* 47(6): 1001–1003 (1988).
Chen et al., Cornstarch therapy in type I glycogen–storage disease, *New England J. Medicine,* 310(3): 171–174 (1984).
Dawson, DCCT and primary care prescription for change, *Clin. Diabetes,* 11: 88–96 (1993).
Glaser et al., Persistent hyperinsulinemic hypoglycemia of infancy: Long–term octreotide treatment without pancreatectomy *J. Pediatrics,* 123:644–650 (1993).
Goldberg et al.; Nutrition therapy for hepatic glycogen storage diseases,*Journal of the American Dietetic Association* 93(12): 1423–1430 (Dec. 1993).
Hengesh, Drugs affecting sugar metabolism, *Princ. Medicinal Chemistry,* (W. Foye 3rd ed.), pp. 531–550 (1989).
Kaufman et al., A randomized crossover, ,blinded trail of uncooked cornstarch to diminish nocturnal hypoglycemia at diabetes camp,*J. Inv. Med.,* 43, Supp. 1, p. 188A (1995).
Lozano et al., Cornstarch ingestion after oral glucose loading: effect on glucose concentrations, hormone response, and symptoms in patients with postprandial hypoglycemic syndrome, *Am. J. Clin. Nutr.,* 52: 667–670 (1990).
Murphy, Just a spoonful of cornstarch . . . , *Magazine of Children's Hospital of Los Angeles,* Winter 94/95, pp. 5–7.
Ogata et al., Effect of cornstarch formula in an infant with type I glycogen storage disease, *Acta Paediatrica Japonica,* 30, (5): 547–552 (1988).
Simpson et al., Food physical factors have different metabolic effects in nondiabetics and diabetics,*Am. J. Clin. Nutr.,* 42: 462–469 (1985).
Smit et al., The dietary treatment of children with type I glycogen storage disease with slow release carbohydrate, *Pediatric Research,* 18(9): 879–881 (1984).
Ververs et al., Complex carbohydrates in the prevention of nocturnal hypoglycaemia in diabetic children, *European J. Clin. Nutr.,* 47(4): 268–273 (1993).
Wiesenfeld et al., Effect of dietary carbohydrate and phenotype on sucrase, maltase, lactase, and alkaline phosphatase specific activity in SHR/N–cp rat, *Proc. Soc. Exp. Biol. & Med.,* 202:(3): 338–344 (1993).
Wolfsdorf et al. Optimal daytime feeding regimen to prevent postprandial hypoglycemia in type I glycogen storage disease, *Am. J. Clin. Nutr.,* 56: 587–592 (1992).
Wolfsdolf et al., Physical growth and development of children with type I glycogen–storage disease: comparison of the effects of long–term use of dextrose and uncooked cornstarch, *Am. J. Clin. Nutr.,* 52: 1051–1057 (1990).
International Search Report, PCT/US/21082; Date of Mailing; Feb. 21,2001.

* cited by examiner

Primary Examiner—Elli Peselev
(74) *Attorney, Agent, or Firm*—Myers Bigel Sibley & Sajovec, P.A.

(57) ABSTRACT

A method of suppressing appetite in a subject in need thereof comprises administering to said subject, in an effective appetite suppressing amount, a food composition that includes a slowly absorbed complex carbohydrate such as uncooked cornstarch. A method of enhancing exercise performance or recovery in a subject in need thereof comprises administering to said subject, in an amount effective to enhance exercise performance or recovery, a food composition that includes a slowly absorbed complex carbohydrate such as uncooked cornstarch.

40 Claims, 1 Drawing Sheet

METHODS FOR SUPPRESSING APPETITE AND ENHANCING EXERCISE AND RECOVERY

FIELD OF THE INVENTION

The present invention concerns nutritional supplements or food compositions that are useful for suppressing appetite and for enhancing exercise performance and recovery.

BACKGROUND OF THE INVENTION

Increased longevity in the human population and increased costs of health care have generated considerable interest in alternatives to conventional therapies. Drug therapies are considered a desirable alternative to surgical treatments whenever possible because of the cost savings involved. However, drug therapy can itself become expensive. As a result, there is a need for still other approaches, such as nutritional therapies, for various disorders.

U.S. Pat. No. 5,420,107 to Brooks describes a food supplement containing lactic acid salts and/or polymers as an energy source supplement during exercise and recovery.

U.S. Pat. No. 5,843,921 to Kaufman describes a therapeutic food composition that contains a slowly digested complex carbohydrate, particularly uncooked cornstarch, useful for diminishing blood sugar fluctuations in diabetic patients, and particularly as a night time snack food.

U.S. Pat. No. 5,866,555 to Bell et al. describes a diabetic supplement bar that preferably contains uncooked cornstarch,.

U.S. Pat. No. 5,902,797 to Bell et al. describes a nutritional supplement bar used to treat appetite suppression and combat weight loss.

SUMMARY OF THE INVENTION

A first aspect of the present invention is a method of suppressing appetite in a subject in need thereof. The method comprises administering to the subject, in an effective appetite suppressing amount, a food composition that includes a slowly absorbed complex carbohydrate such as uncooked cornstarch.

A second aspect of the present invention is a method of enhancing exercise performance or recovery in a subject in need thereof, comprising administering to said subject, in an amount effective to enhance exercise performance or recovery, a food composition that includes a slowly absorbed complex carbohydrate such as uncooked cornstarch.

A food composition or nutritional supplement useful for carrying out the foregoing methods typically comprises:

(a) about 10 to 75 percent by weight of slowly absorbed complex carbohydrate;
  (b) about 10 to 40 percent by weight of rapidly absorbed complex carbohydrate;
  (c) about 2 to 40 percent by weight of protein;
  (d) about 2 to 40 percent by weight of fat; and
  (e) at least one sweetening agent in an amount effective to sweeten said food composition.

Numerous other additives, supplements and the like can also be included in the composition, as desired.

The foregoing and other objects and aspects of the present invention are explained in detail in the drawings herein and the specification set forth below.

DETAILED DESCRIPTION OF PREFERRED EMBODIMENTS

Figure 1:
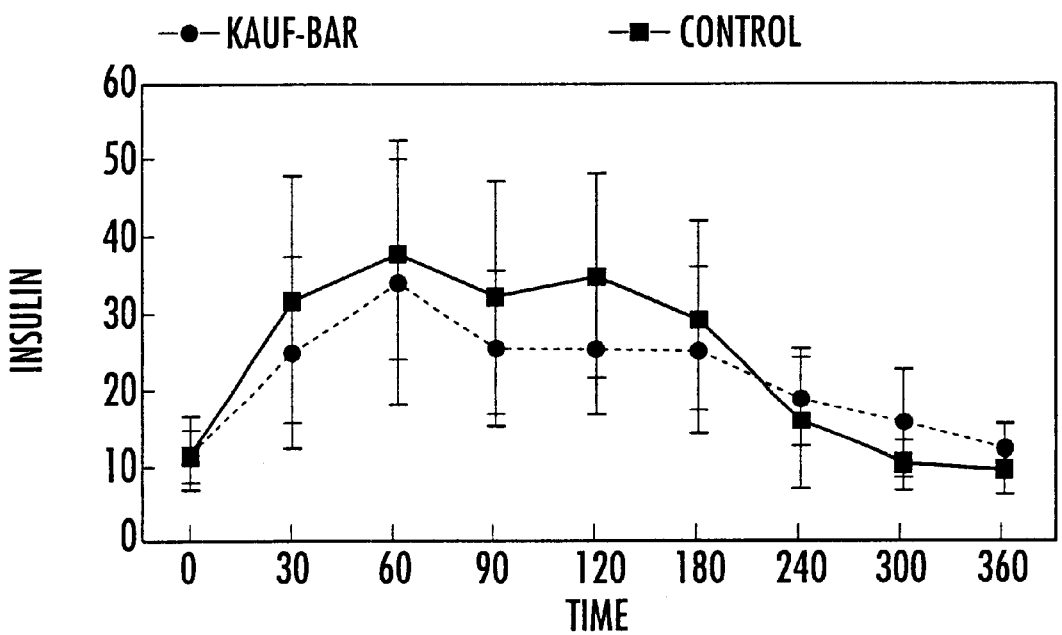
FIG. 1 shows blood insulin levels over time for patients administered a food composition of the invention as compared to a control.

The term "complex carbohydrates" as used herein refers to macromolecular carbohydrates including starches, polydextrose and other polysaccharides.

The term "sweetening agent" refers to simple sugars (e.g., sucrose, lactose, galactose and fructose), sugar alcohols used as sweeteners (e.g., sorbitol or maltitol) and artificial sweeteners (e.g., aspartame, sodium saccharin and acesulfame potassium).

The term "nutrients" as used herein refers to carbohydrates, proteins and fats.

1. Food compositions.

In general, a food composition used to carry out the present invention typically comprises:

a) a complex carbohydrate which is slowly absorbed from the human gastrointestinal tract (hereinafter "slowly absorbed carbohydrate"), i.e., is slowly digested and is not completely metabolized even after 3–4 hours;
  b) optionally, but preferably, a complex carbohydrate which is more rapidly absorbed from the digestive tract (hereinafter "rapidly absorbed carbohydrate");
  c) optionally, but preferably, protein;
  d) optionally, but preferably, fat; and
  e) optionally, but preferably, at least one sweetening agent.

Food compositions that may be used to carry out the present invention are described in greater detail below. In general, food compositions that may be used to carry out the present invention include those described in U.S. Pat. No. 5,843,921 to Kaufman, subject to the proviso that it is not critical that the amount of simple sugars other than fructose in the composition be less than about 3 grams per unit as stated therein. Food compositions that may be used to carry out the present invention further include those described in U.S. Pat. No. 5,866,555 to Bell et al. and U.S. Pat. No. 5,902,797 to Bell et al., taking note that the complex carbohydrate is therein indicated as preferably a slowly absorbed complex carbohydrate, uncooked cornstarch, as described in U.S. Pat. No. 5,843,921 to Kaufman (applicant specifically intends that the disclosures of all U.S. Patent references cited herein be incorporated herein by reference in their entirety).

The ingredients in the food composition may include any conventional food ingredients of adequate purity and wholesomeness which preferably supply the desired amounts of total calories and percentage of calories from carbohydrates, protein and fat, respectively, and wherein the relative weight ranges of slowly absorbed carbohydrates, rapidly absorbed carbohydrates, protein, fat and fructose are as indicated previously. In the preferred embodiment of a snack-type bar, the ingredients may include, by way of illustration, uncooked cornstarch as the slowly absorbed carbohydrate; polydextrose, peanuts, peanut derivatives (e.g., peanut butter), other nuts or nut derivatives as sources of rapidly absorbed carbohydrates, fat and protein; and other protein sources such as soy protein, whey protein, and casein hydrolysate. Artificial sweeteners (e.g., aspartame or saccharin) may be included in the food composition in small amounts, but fructose and/or sorbitol and maltitol (3–15 grams) are the principal sweeteners. Coloring agents, water, salt, preservatives and other standard ingredients or additives normally used in the preparation of a snack or candy-type bar may be utilized, as well as up to 3 grams of simple sugars other than fructose (e.g., sucrose, lactose or galactose), provided that the total nutrient and calorie profile of the finished bar or other form of the novel food composition comes within the parameters defined above.

Uncooked cornstarch is the preferred source of slowly absorbed carbohydrate for purposes of the invention since its carbohydrate content and its rate of metabolism are known and are relatively uniform, and it may be readily formulated into a variety of palatable food compositions.

In one embodiment, the food composition preferably contains about 20 to about 50 grams of nutrients per serving or unit, e.g., per bar, including: about 15–35 grams of total carbohydrates (about 5–15 grams of slowly absorbed complex carbohydrate, about 7–20 grams of rapidly absorbed complex carbohydrate and about 0–15 grams of simple sugar, sugar alcohol, or combination thereof; about 3–20 grams of protein; and about 2–7 grams of fat).

In one embodiment, the food composition preferably provides about 100–230 calories per serving or unit, of which: about 50–75% are from slowly absorbed and rapidly absorbed complex carbohydrates; about 10–25% are from protein; and about 10–25% are from fat.

The food composition containing the foregoing components may be in any conventional "snack" form, e.g., bars, puddings, cookies, wafers, milkshakes, gels and the like, contained within a suitable package such as a bottle, can or wrapper. The food composition may be an extruded, non-baked food product. Snack-type bars resembling candy or granola bars, or rapidly consumable packaged gels, are most convenient for storage, handling and administration purposes and, when produced with scores, perforations or grooves thereon, can be easily divided for purposes of administering a fraction of a bar where appropriate. Gels may be provided as an essentially homogeneous composition in a squeezable consumable package like a tooth-paste container to be squeezed directly from the package into the mouth for consumption.

The food composition may have a weight of 10 to 200 grams, depending upon the manner of packaging and intended manner of administration. As noted above, the composition may be designed with scores or the like to divide the composition for administration, or the composition may be administered in two or more units of the discrete products.

2. Methods of treatment.

Subjects that may be treated by the methods described herein are typically human subjects. The subjects may be normal subjects (that is, patients not afflicted with diabetes) or may be subjects afflicted with diabetes. The subjects may be of any age, including juvenile, adolescent and adult, with the dosage or amount of the food composition administered adjusted appropriately.

The present invention may be used to suppress appetite in a subject in need thereof. Such subjects may include obese patients, patients with diabetes in whom weight loss is a specific part of the diabetes treatment plan, patients at risk of weight gain due to a transient event such as recovery from an injury, surgery or the like, and individuals who desire to lose weight or maintain an existing weight.

The present invention may also be used to enhance exercise performance or recovery (e.g., reduce fatigue after exercise) in a subject in need thereof (e.g., an exercising subject). The method is useful in conjunction with a variety of exercises, including swimming, walking, running, cycling, weight lifting, stationary aerobic exercises, etc. The exercise may be an aerobic exercise or an anaerobic exercise. The exercise may be an endurance exercise (that is, extending more than one-half hour or one hour in length). Any subject may utilize the nutritional supplements described herein, including trained or conditioned athletes (i.e., individuals who have conditioned themselves to the point of having a low resting blood pressure and pulse; typically with a diastolic pressure less than 80 or 70 mmHg, and a heart rate less than 60 beats per minute).

The composition is typically administered in an amount ranging from 10 to 200 grams per serving, depending upon the age, weight and condition of the subject. 1, 2, 3, or even 4 or more servings may be administered per day, again depending upon the conditions of the subject and the purpose of the treatment. For example, where used to suppress appetite, the composition may be administered as a meal replacement or as a before-meal or between-meal snack. Where the composition is administered to enhance exercise performance or recovery, the composition may be consumed on multiple occasions throughout the course of the exercise event.

The present invention is explained in greater detail in the following non-limiting Examples.

EXAMPLE 1

Appetite Suppression

Figure 2:
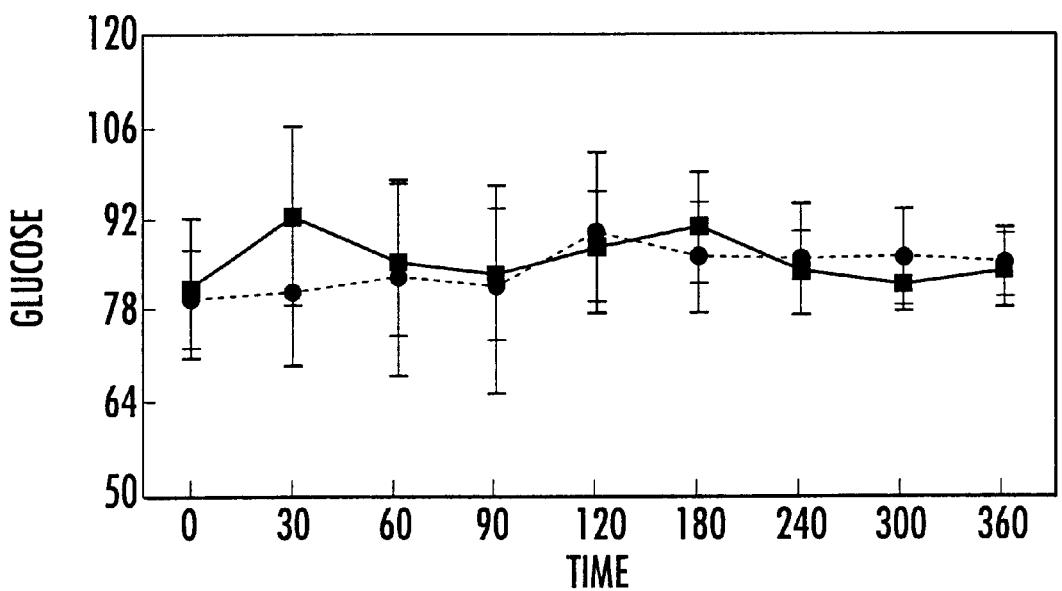
FIG. 2 shows blood glucose levels over time for patients administered a food composition of the invention, as compared to a control.

Ten normal subjects ingested on two occasions 75 grams of carbohydrate in the form of 2½ snack bars (one with uncooked cornstarch and the other with the same calories and carbohydrates but without uncooked cornstarch; ingredients included 5 grams protein and 3 grams fat/bar=active bar versus placebo bar with the same ingredients for a total of 22 grams of carbohydrate but without uncooked cornstarch). Detailed analysis as shown in FIG. 1 showed that there was a significant decrease in the insulin peak at 30 minutes and 120 minutes with cornstarch bar ingestion (in addition to complex carbohydrate, fat and protein) compared to a non-cornstarch bar meal of comparable carbohydrate, fat and protein, but without cornstarch. There was no difference in the area under the curve for insulin levels between these two meals showing that there were equivalent amounts of carbohydrate absorbed. As shown in FIG. 2, there was also a higher blood glucose peak with the non-cornstarch meal versus the cornstarch meal at 30 minutes. The reverse was true at 300 minutes, when the blood glucose level was statistically higher at 300 minutes with the cornstarch bar compared to the non-cornstarch bar.

These data indicate that the cornstarch bar has a low glycemic index (and therefore is an appetite suppressant) by showing that in normal subjects the ingestion of the food bar with cornstarch is associated with a slower rise, a decreased peak value, and a more gradual decrease in blood glucose and insulin levels when compared to bars without cornstarch.

EXAMPLE 2

Exercise Performance

Fifteen subjects with diabetes, on two separate occasions, ingested 30 grams of carbohydrate in the form of 1 snack bar (one with uncooked cornstarch the other with the same calories and charbohydrates but without cornstarch ingredients included 5 grams protein and 3 grams fat/bar=active bar versus placebo bar with the same ingredients for a total of 30 grams of carbohydrate but without uncooked cornstarch).

Subjects perform a standardized exercise regimen consisting of 30 minutes of vigorous exercise 2 and ½ hours after ingesting the bar.

Analysis showed that there was a significant decrease in the frequency of hypoglycemia at the end of exercise after ingestion of the cornstarch containing bar compared to the non-cornstarch bar.

These data indicate that the cornstarch bar has a low glycemic index (and therefore is slowly released into the blood stream) and is associated with enhanced carbohydrate utilization during and after exercise.

The foregoing is illustrative of the present invention, and is not to be construed as limiting thereof. The invention is defined by the following claims, with equivalents of the claims to be included therein.

I claim:

1. A method of suppressing appetite in a subject in need thereof, wherein said subject is healthy, the method comprising administering to said subject, in an effective appetite suppressing amount, a food composition comprising:
    (a) about 10 to 75 percent by weight of slowly absorbed complex carbohydrate;
    (b) about 10 to 40 percent by weight of rapidly absorbed complex carbohydrate;
    (c) about 2 to 40 percent by weight of protein;
    (d) about 2 to 40 percent by weight of fat; and
    (e) at least one sweetening agent in an amount effective to sweeten said food composition;
    wherein the amount of simple sugars other than fructose in said composition is less than about 3 grams.

2. A method of suppressing appetite in a subject in need thereof, wherein said subject does not have diabetes, the method comprising administering to said subject, in an effective appetite suppressing amount, a food composition comprising:
    (a) about 10 to 75 percent by weight of slowly absorbed complex carbohydrate;
    (b) about 10 to 40 percent by weight of rapidly absorbed complex carbohydrate;
    (c) about 2 to 40 percent by weight of protein;
    (d) about 2 to 40 percent by weight of fat; and
    (e) at least one sweetening agent in an amount effective to sweeten said food composition;
    wherein the amount of simple sugars other than fructose in said composition is less than about 3 grams.

3. A method of suppressing appetite in a subject in need thereof, wherein said subject is obese and does not have diabetes, the method comprising administering to said subject, in an effective appetite suppressing amount, a food composition comprising:
    (a) about 10 to 75 percent by weight of slowly absorbed complex carbohydrate;
    (b) about 10 to 40 percent by weight of rapidly absorbed complex carbohydrate;
    (c) about 2 to 40 percent by weight of protein;
    (d) about 2 to 40 percent by weight of fat; and
    (e) at least one sweetening agent in an amount effective to sweeten said food composition;
    wherein the amount of simple sugars other than fructose in said composition is less than about 3 grams.

4. A method of enhancing exercise performance of recovery in a subject in need thereof, wherein said subject is healthy, the method comprising administering to said subject, in an effective appetite suppressing amount, a food composition comprising:
    (a) about 10 to 75 percent by weight of slowly absorbed complex carbohydrate;
    (b) about 10 to 40 percent by weight of rapidly absorbed complex carbohydrate;
    (c) about 2 to 40 percent by weight of protein;
    (d) about 2 to 40 percent by weight of fat; and
    (e) at least one sweetening agent in an amount effective to sweeten said food composition;
    wherein the amount of simple sugars other than fructose in said composition is less than about 3 grams.

5. A method of enhancing exercise performance of recovery in a subject in need thereof, wherein said subject does not have diabetes, the method comprising administering to said subject, in an effective appetite suppressing amount, a food composition comprising:
    (a) about 10 to 75 percent by weight of slowly absorbed complex carbohydrate;
    (b) about 10 to 40 percent by weight of rapidly absorbed complex carbohydrate;
    (c) about 2 to 40 percent by weight of protein;
    (d) about 2 to 40 percent by weight of fat; and
    (e) at least one sweetening agent in an amount effective to sweeten said food composition;
    wherein the amount of simple sugars other than fructose in said composition is less than about 3 grams.

6. The method of claim 5, wherein said subject is obese.

7. A method according to claim 2, wherein said slowly absorbed complex carbohydrate is uncooked cornstarch.

8. A method according to claim 2, wherein said sweetening agent includes about 10 to 60 percent by weight of a simple carbohydrate selected from the group consisting of sucrose, glucose, dextrose, and combinations thereof.

9. A method according to claim 2, wherein said sweetening agent includes about 2 to 60 percent by weight of a sugar alcohol selected from the group consisting of sorbitol, maltitol and combinations thereof.

10. A method according to claim 2, wherein said sweetening agent includes about 2 to 60 percent by weight of fructose.

11. A method according to claim 2, wherein the amount of simple sugars other than fructose in said composition in less than about 40 percent by weight.

12. A method according to claim 2, wherein said sweetening agent is selected from the group consisting of aspartame, sodium saccharin and acesulfame potassium.

13. A method according to claim 2, wherein said food composition is in the form of a snack bar, pudding, cookie, wafer, milkshake or gel.

14. A method according to claim 2, wherein said food composition has a weight of 10 to 200 grams.

15. A method according to claim 5, wherein said food composition is administered prior to exercise by said subject.

16. A method according to claim 5, wherein said exercise is aerobic exercise.

17. A method according to claim 5, wherein said exercise is an endurance exercise.

18. A method according to claim 2, wherein said food composition is in the form of a snack bar.

19. A method according to claim 18, wherein said slowly absorbed complex carbohydrate is uncooked cornstarch and said rapidly absorbed complex carbohydrate is provided by an ingredient selected from the group consisting of polydextrose, nuts, and nut derivatives.

20. A method according to claim 19, wherein said nut or nut derivatives are peanuts or peanut derivatives.

21. A method according to claim 2, wherein said food composition comprises per unit or serving about 20 to 50 grams of nutrients per serving or unit, including about 15–35 grams of total carbohydrate.

22. A method according to claim 2, wherein said food composition comprises, per unit or serving, about 20 to 50 grams of nutrients, including:
- (a) about 5 to 15 grams of slowly absorbed complex carbohydrate,
- (b) about 7–20 grams of rapidly absorbed complex carbohydrate,
- (c) about 0–15 grams of simple sugar, sugar alcohol, or combinations thereof,
- (d) about 3–20 grams of protein, and
- (e) about 2–7 grams of fat.

23. A method according to claim 2, wherein said food composition is served as a meal replacement.

24. A method according to claim 5, wherein said food composition is administered throughout the course of an exercise event by said subject.

25. A method according to claim 5, wherein said food composition is administered during exercise by said subject.

26. A method according to claim 5, wherein said food composition is administered after exercise by said subject.

27. A method according to claim 5, wherein said slowly absorbed complex carbohydrate is uncooked cornstarch.

28. A method according to claim 5, wherein said sweetening agent includes about 10 to 60 percent by weight of a simple carbohydrate selected from the group consisting of sucrose, glucose, dextrose, and combinations thereof.

29. A method according to claim 5, wherein said sweetening agent includes about 2 to 60 percent by weight of a sugar alcohol selected from the group consisting of sorbitol, maltitol, and combinations thereof.

30. A method according to claim 5, wherein said sweetening agent includes about 2 to 60 percent by weight of fructose.

31. A method according to claim 5, wherein the amount of simple sugars other than fructose in said composition is less than about 40 percent by weight.

32. A method according to claim 5, wherein said sweetening agent is selected from the group consisting of aspartame, sodium saccharin and acesulfame potassium.

33. A method according to claim 5, wherein said food composition is in the form of a snack bar, pudding, cookie, wafer, milkshake or gel.

34. A method according to claim 5, wherein said food composition has a weight of about 10 to 200 grams.

35. A method according to claim 5, wherein said food composition is in the form of a snack bar.

36. A method according to claim 35, wherein said slowly absorbed complex carbohydrate is uncooked cornstarch and said rapidly absorbed complex carbohydrate is provided by an ingredient selected from the group consisting of polydextrose, nuts, and nut derivatives.

37. A method according to claim 36, wherein said nut or nut derivatives are peanuts or peanut derivatives.

38. A method according to claim 5, wherein said food composition comprises per unit or serving about 20 to 50 grams of nutrients per serving or unit, including about 15–35 grams of total carbohydrate.

39. A method according to claim 5, wherein said food composition comprises, per unit or serving, about 20 to 50 grams of nutrients, including:
- (a) about 5 to 15 grams of slowly absorbed complex carbohydrate,
- (b) about 7–20 grams of rapidly absorbed complex carbohydrate,
- (c) about 0–15 grams of simple sugar, sugar alcohol, or combinations thereof,
- (d) about 3–20 grams of protein, and
- (e) about 2–7 grams of fat.

40. The method of claim 1, wherein the subject is not a diabetic subject.

* * * * *

UNITED STATES PATENT AND TRADEMARK OFFICE
CERTIFICATE OF CORRECTION

PATENT NO.    : 6,534,487 B1                                          Page 1 of 1
DATED         : March 18, 2003
INVENTOR(S)   : Kaufman It is certified that error appears in the above-identified patent and that said Letters Patent is hereby corrected as shown below:

Title page,
Item [56], References Cited, U.S. PATENT DOCUMENTS, add the following references: -- 6,156,738    12/2000    Bell et al.    514/60 --
FOREIGN PATENT DOCUMENTS, add the following references:
-- EP    0749697A1    12/1996    A23P/1/08 --

Signed and Sealed this

Ninth Day of December, 2003

JAMES E. ROGAN
*Director of the United States Patent and Trademark Office*